(12) United States Patent
Hanks

(10) Patent No.: US 6,244,862 B1
(45) Date of Patent: Jun. 12, 2001

(54) ORTHODONTIC APPLIANCE

(76) Inventor: Stephen Hanks, 788 Rossmore, Las Vegas, NV (US) 89110

( * ) Notice: Subject to any disclaimer, the term of this patent is extended or adjusted under 35 U.S.C. 154(b) by 0 days.

(21) Appl. No.: 09/569,659

(22) Filed: May 12, 2000

Related U.S. Application Data

(60) Provisional application No. 60/136,623, filed on May 27, 1999.

(51) Int. Cl.[7] .................................................. A61C 3/00
(52) U.S. Cl. ............................................................ 433/19
(58) Field of Search ................................. 433/6, 18, 19

(56) References Cited

U.S. PATENT DOCUMENTS

| | | | |
|---|---|---|---|
| 4,551,095 | * 11/1985 | Mason | 433/19 |
| 5,632,618 | * 5/1997 | Jensen | 433/19 |
| 5,879,157 | * 3/1999 | Scheu | 433/19 |
| 5,919,042 | * 7/1999 | Williams | 433/19 |

* cited by examiner

Primary Examiner—Nicholas D. Lucchesi
(74) Attorney, Agent, or Firm—Philip J. Anderson; Anderson & Morishita L.L.C.

(57) ABSTRACT

An orthodontic appliance and kit adapted to provide Herbst therapy as well as arch development. The appliance includes mandibular and maxillary components to be attached to the teeth, each component having a threaded bore. For Herbst therapy, telescoping links are connected between the components with screw hubs threadably received by the threaded bores. For arch development, expansion mechanisms are provided on the components.

10 Claims, 12 Drawing Sheets

DIAGRAM A

ZERO OVERBITE=ZERO OVERJET=
NO MANDIBULAR RETRUSION

DIAGRAM B

30% OVERBITE=4-5MM OVERJET=
MANDIBULAR RETRUSION

DIAGRAM C

70% OVERBITE=6-8MM OVERJET=
MORE MANDIBULAR RETRUSION

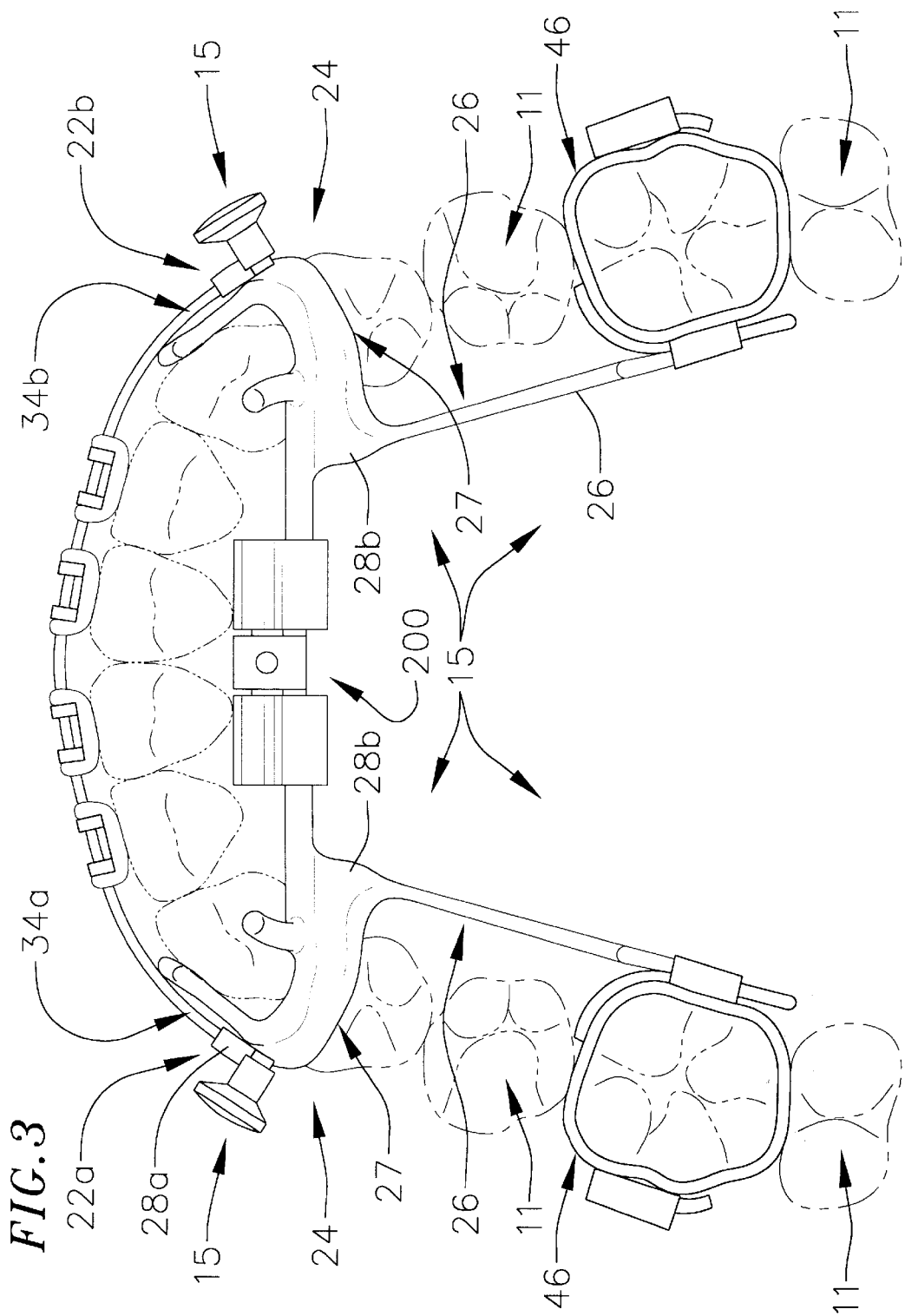

ORTHODONTIC APPLIANCE

This application claims benefit of Ser. No. 60/136623 filed May 27, 1999.

FIELD OF THE INVENTION

The present invention relates to an appliance and kit for providing Herbst therapy as well as arch development to correct certain orthodontic misalignments including horizontal and vertical overbite.

BACKGROUND

Devices for treatment of orthodontic overbite have been proposed. In the early 1900's, German orthodontic practitioners were well aware of the efficacy of incline planes to resolve overjets (overbite). As approximation of the teeth occurred, the inclined plane attached to the mandible contacted the inclined plane of the maxilla. As closure progressed, the lower jaw was forced into a protruded position as dictated by the inclines. Since correction of the overjet depended on constant protrusion of the mandible to effect cellular changes required to eventually result in the new and desired lower jaw position, it was necessary that patients so treated hold the teeth in constant contact. Holding teeth in the contact position required constriction of the muscles which protrude the lower jaw (pterygoids), whereas relaxation of those muscles resulted in the teeth losing contact and the lower jaw being allowed to retreat to its former position. With the jaw in its former position, no orthopedic cellular change and hence no permanent overjet correction would be realized.

Emil Herbst, in his early 1900 work "Zahnarztliche Orthopadie" stated:

"When many unsuccessful results through the use of inclined planes occurred, the reason was that many patients avoided the "stressed" position. Instead of holding their teeth closed or in contact with the inclined plane and allowing (or forcing) the muscles to function, it was more comfortable to hold the mouth open and avoid the strain . . . , that an incline plane can only be effective, when the teeth are truly in contact, and that on the other hand, many patients, especially uncooperative, lazy or unmotivated children, relax muscle pressure by holding the mouth open, I constructed a guide that would work against this relaxation (from holding the mouth open)."

It is reasonable to conclude that if an inclined plane in one direction eliminates an overjet, an inclined plane in the opposite direction may create or exacerbate an overjet. By "adverse inclined plane" what is meant is an inclined plane in the reverse direction. In the mouth there is a naturally occurring adverse inclined plane. That inclined plane is the relationship of the lower incisor tips in contact with the lingual surfaces of the upper incisors. FIG. 1 shows how increasing overbite results in increasing overjet or, as in the case of a mandible which has been forward-postured by an inclined plane-type of appliance, how the excess overbite and the contact between the lower incisor tips and the lingual surfaces of the upper incisors, results in retrusion of the mandible forcing it back into its original position thereby reversing those orthopedic changes previously derived.

Additionally overbite orthopedic correction appliances which have been employed have been subject to failure. Appliances for providing Herbst therapy are described in Mason, U.S. Pat. No. 4,551,095, Jones, U.S. Pat. No. 4,462,800 and Kumar, U.S. Pat. No. 5,183,338. The two common sources of failure are metal fatigue and inadequate weld or solderjoints. All oral appliances are subject to the harsh dynamics associated with chewing, speech, and swallowing. During, for example, swallowing, there is motion associated with the lower jaw while the upper and lower jaws are closed together. Humans swallow in excess of 1000 times a day just to lubricate the pharyngeal mucosa. As a result of these oral dynamics, the metal parts of the appliance are stressed and flexed leading to metal fatigue and failure.

It is logical to conclude that by harmonizing the sizes of the components of an appliance, failure as a result of fatigue can be reduced. Further by eliminating or reducing welds, the incidents of failure can be reduced.

BRIEF DESCRIPTION OF THE DRAWINGS

FIG. 3 is a lingual view of the mandibular component of the appliance according to the present invention as installed for Herbst therapy as well as arch development;

FIG. 11B shows a partial section view of the molar band of FIG. 11a;

DESCRIPTION

Figure 2A:
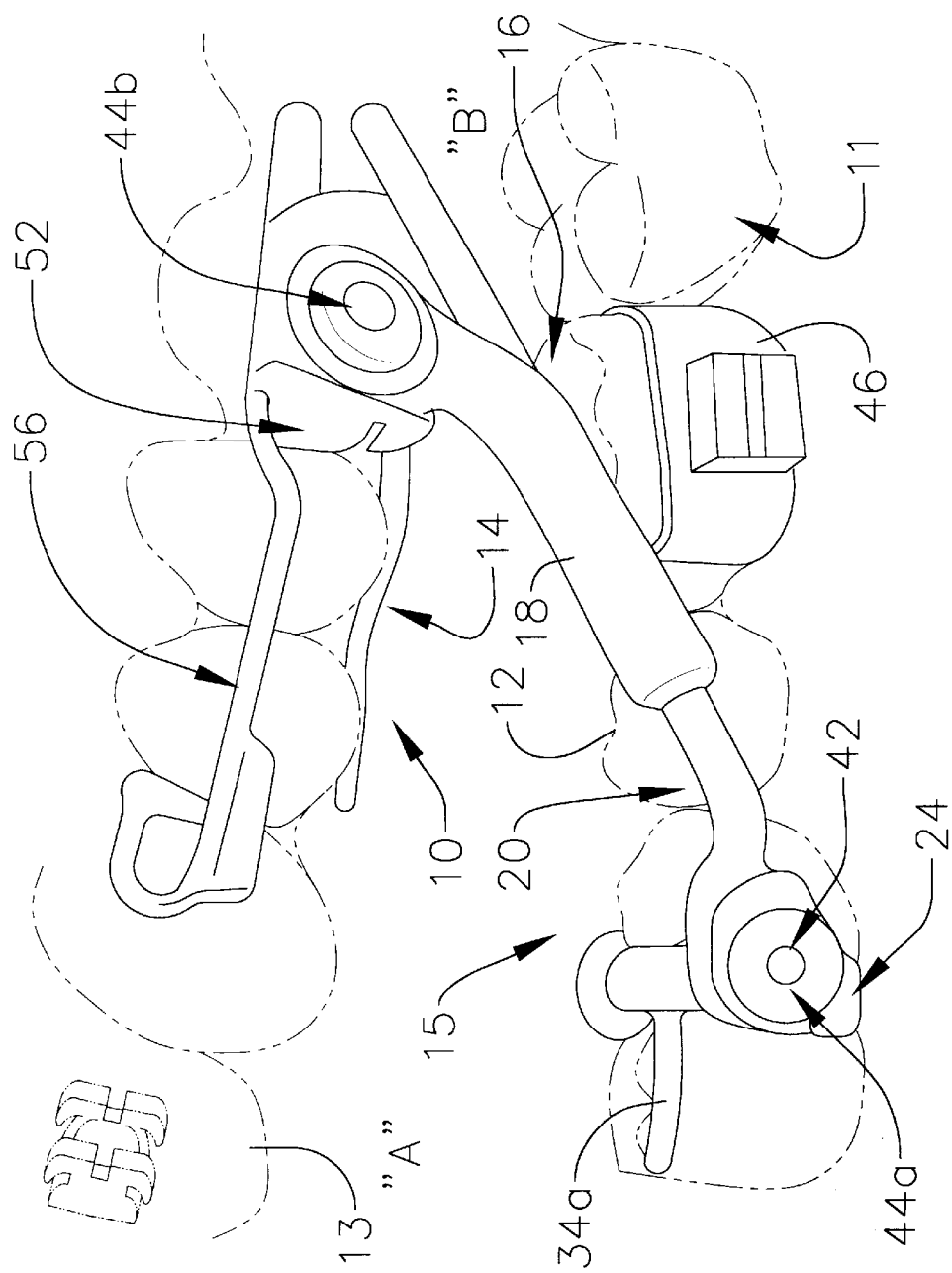
FIG. 2A shows a side view of a portion of the appliance according to the present invention installed in the mouth.

Turning to the drawings, FIGS. 2A, B show portions of the appliance 10 according to the present invention and as positioned in the mouth. As illustrated, the teeth 11 for the mandible 12 are shown as are the maxillary teeth 13. "A" represents the position of the mouth opening and "B" indicates the relative position of the posterior for the mandible 12.

Figure 2B:
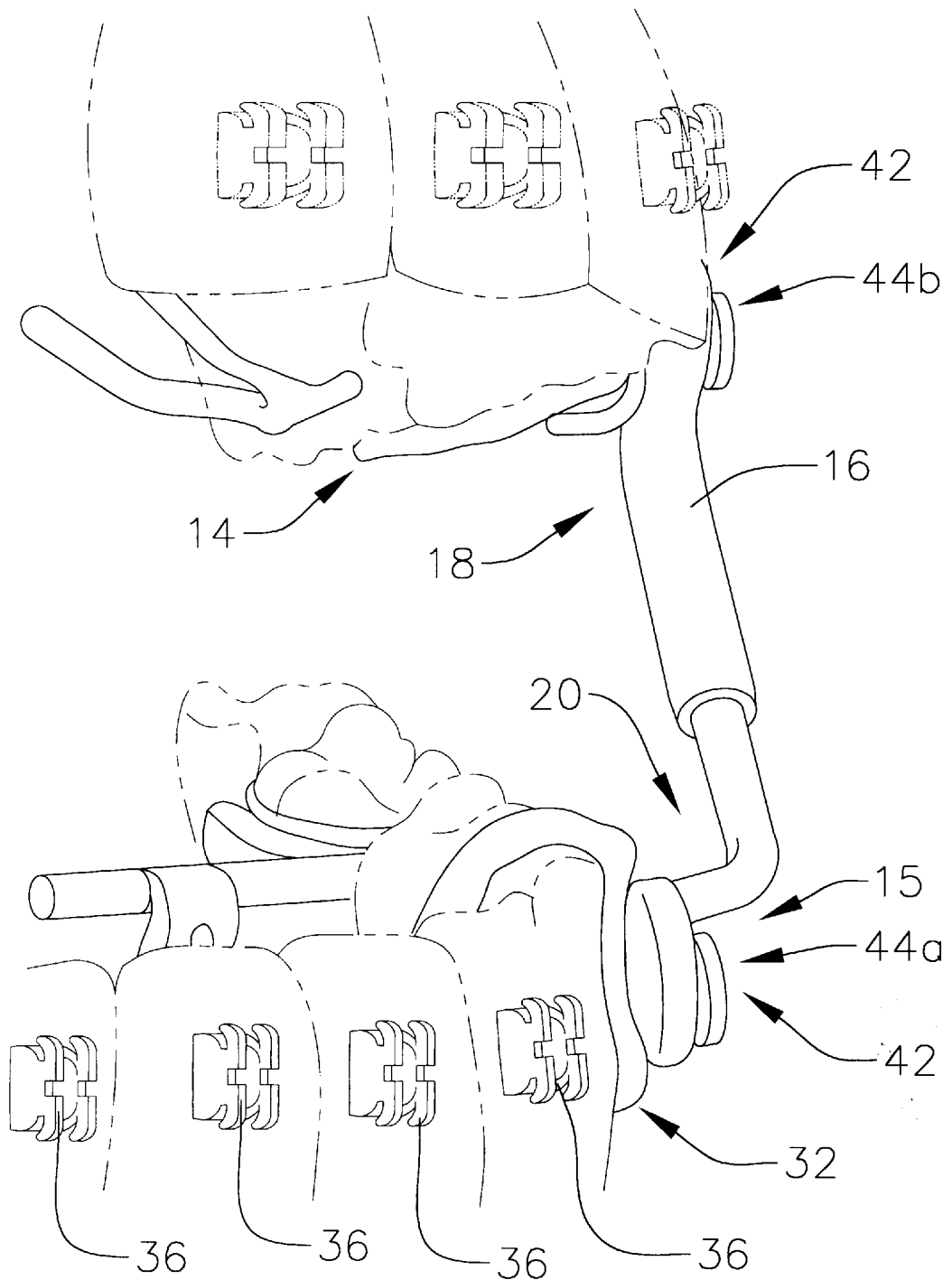
FIG. 2B is a facial view of a portion of the appliance of FIG. 2A.
Figure 7:
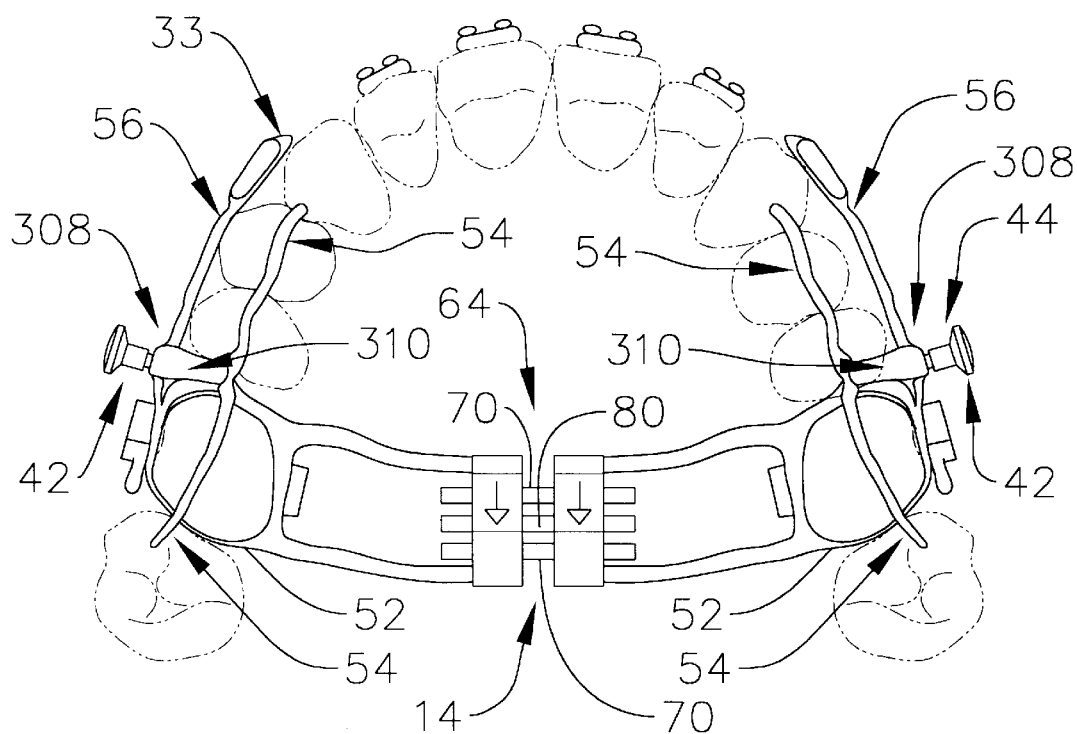
FIG. 7 is an occlusal, installed, view of the maxillary component of the appliance of the present invention.
Figure 8:
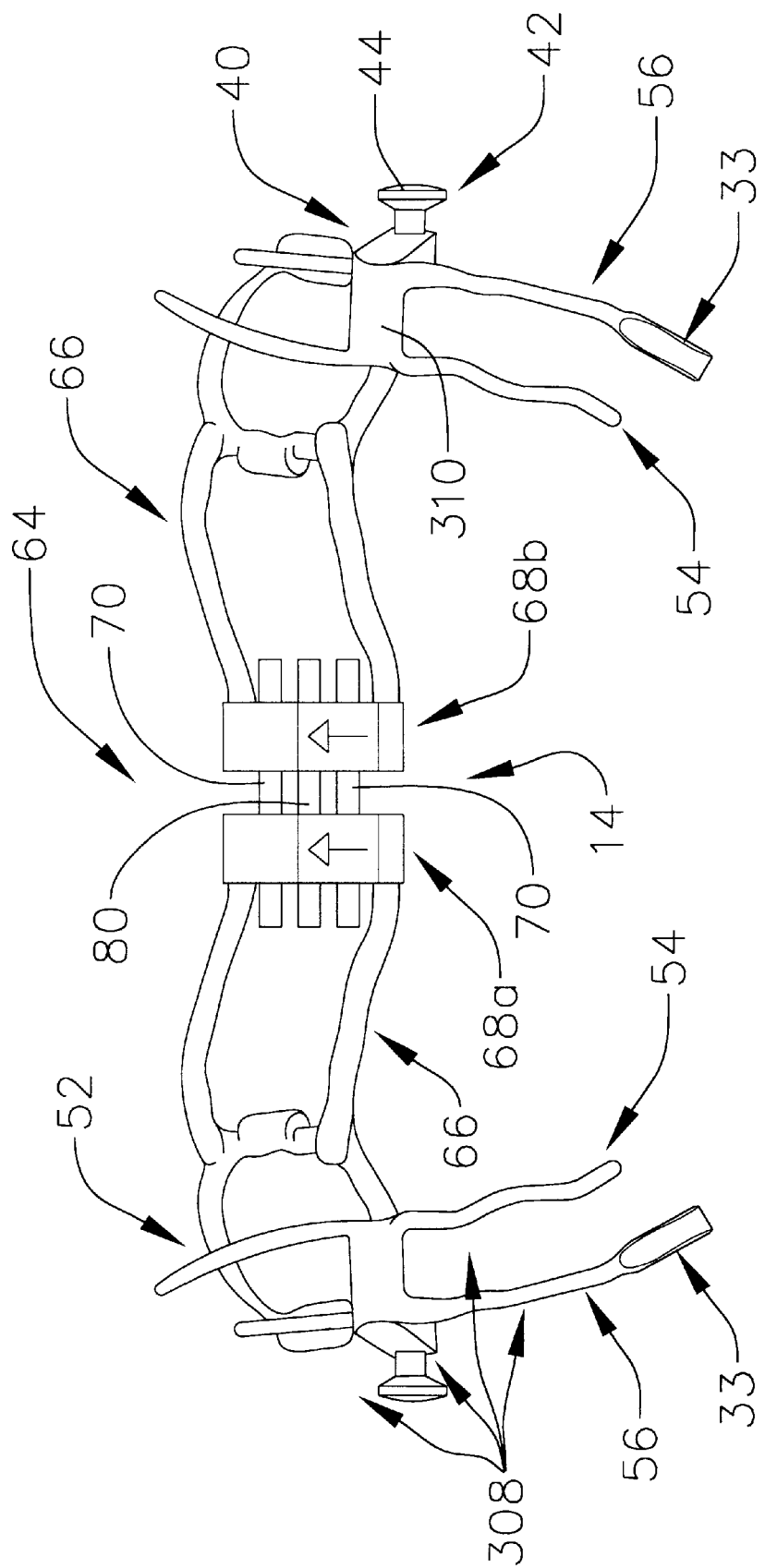
FIG. 8 is an occlusal view of the maxillary component of the appliance of the present invention.
Figure 9:
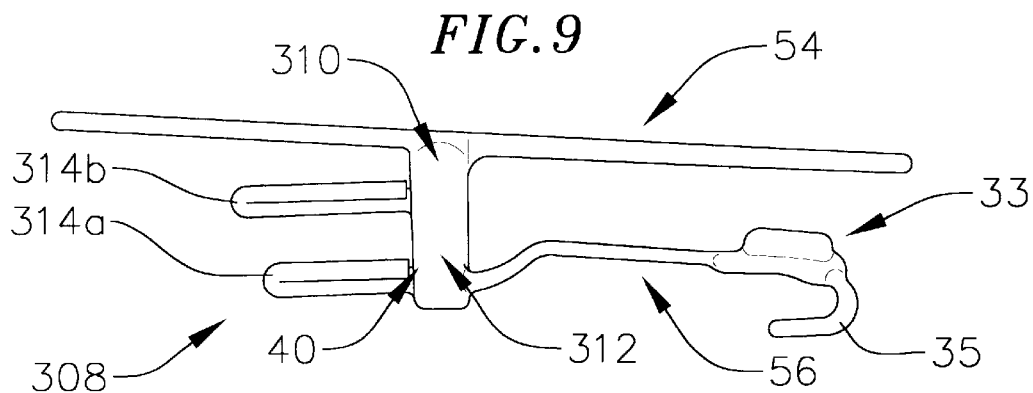
FIG. 9 is a side-occlusal view of a bucco-occlusal segment for the maxillary component.

Broadly stated, appliance 10 includes a maxillary component 14 and a mandibular component 15 shown interconnected by bite controlling rod and tube links 16. As can be appreciated, FIGS. 2A and 2B show only the left side portions of the maxillary and mandibular components 14, 15 and it is to be understood that a like structure would be presented at the right side of the mouth as shown in FIGS. 3 and 7. Further, while only one link 16 is shown it is to be understood that the appliance 10 includes a pair of links 16, each adapted to be positioned at the side of the appliance 10. As will become evident below, the mandibular component 15 supports rods 20 for the links 16 whereas the maxillary component 14 supports receiving tubes 18. It is to be understood that the positions of the tubes 18 and rods 20 could be reversed.

With the appliance 10 assembled in the mouth, Class II discrepancy can be treated by urging the mandible forward as a result of the coupling of the maxillary component 14 and mandibular component 15 by the links 16. Again, while only one link 16 is shown in FIG. 2, it is to be understood that the appliance 10 is symmetrical including links 16 on both sides of the mouth.

Turning to FIGS. 3-6B, the mandibular component 15 is shown. The mandibular component 15 includes left and right buccal segments 22a,b each of which includes an arcuate foot 24 which spans over the teeth 11 from the lingual to the buccal side of the teeth 11. Preferably the feet 24 consist of two lengths of 1.5 mm by 3.0 mm oval wire to lingual ends of which, and at 90 degrees to the long axis, are connected 32 mm lengths of 0.036 inch×0,072 inch oval wire. The oval wire of the feet 24 is bent in the middle over its narrow dimension to approximately 90 degrees to lay over the occlusal tooth surfaces. The apex 27 of the foot 24 lies in the occlusal embrasure between the cuspid and first bicuspid (or first deciduous molar). The buccal and lingual ends 28a, b for each foot 24 are positioned approximate to the facial and lingual gingival between adjacent teeth. From the lingual end 28b of each foot 24 an approximately 32 mm length of 0.036 inch×0.072 inch oval wire defining the lingual extension 26 extends posteriorly from and at 90 degrees to the lingual end 28b of the foot 24 to a position approximating the gingival margins of the buccal teeth.

The buccal segments 22a, b provide support for various components of the mandibular component 15 as well as for wires which connect to braces on the lower front teeth. The buccal segments 22a, b and the remainder of the mandibular component 15 provides for attachment of the links 16 and are adapted to deliver intrusive forces to the anterior teeth which protects against the occurrence of an adverse "reverse" inclined-plane.

Figure 5:
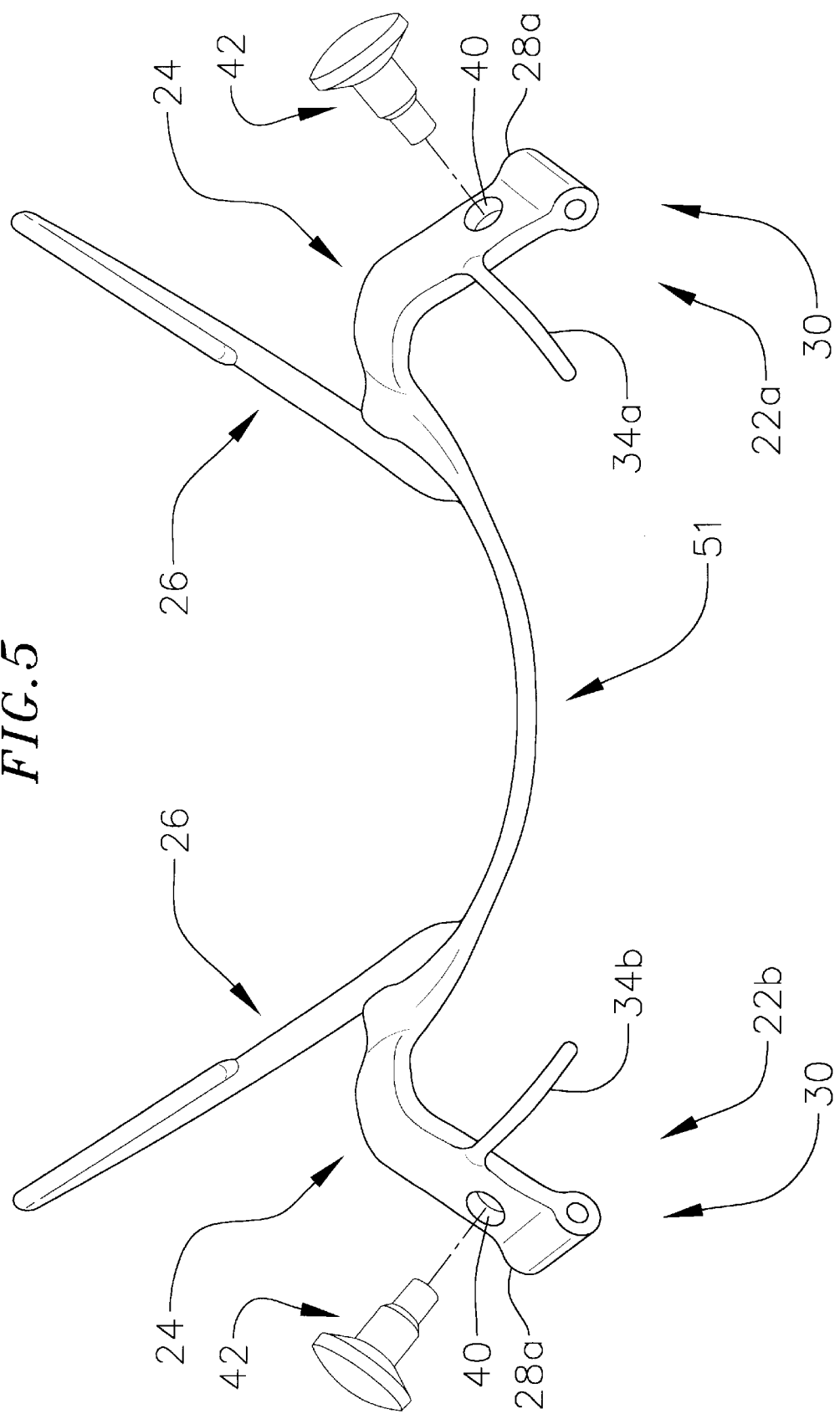
FIG. 5 is a top view of the mandibular component for Herbst therapy alone.
Figure 6A:
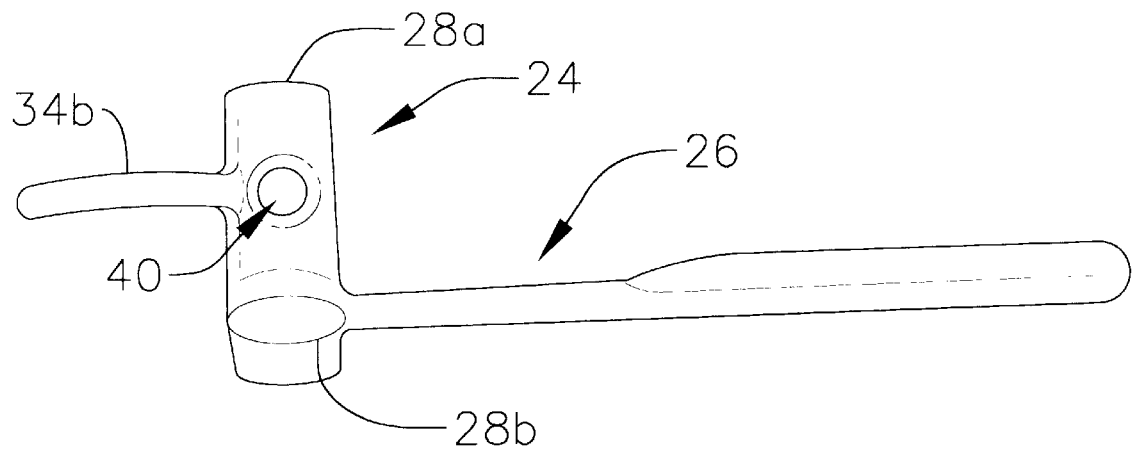
FIG. 6A is a top-side view of a buccal segment of the mandibular component.
Figure 6B:
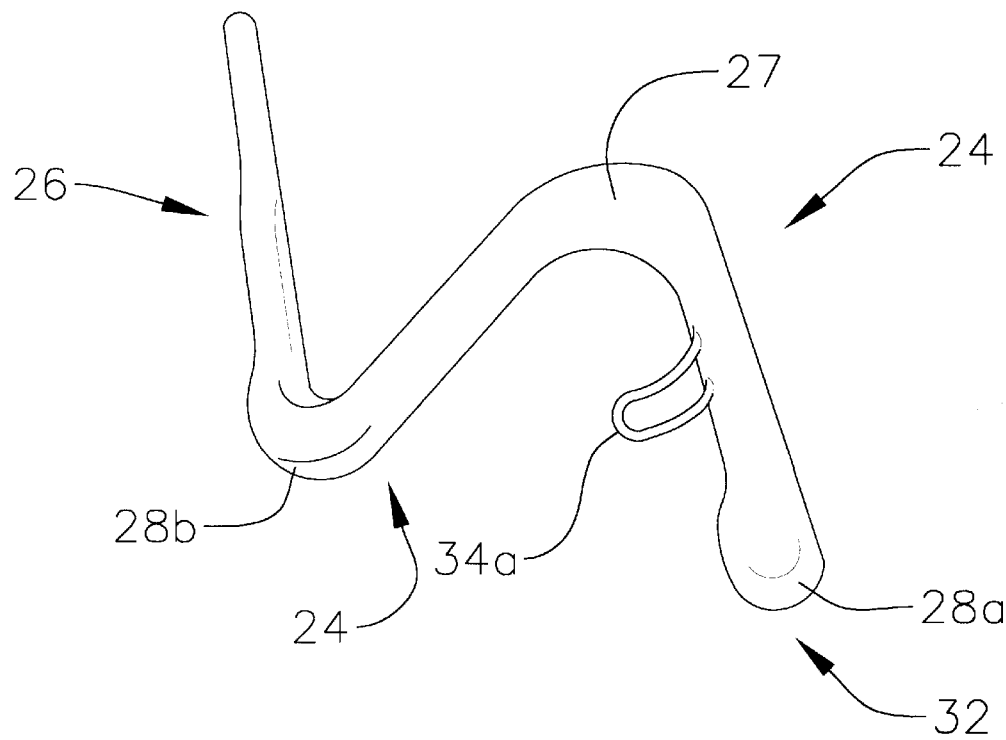
FIG. 6B is a top-front view of the buccal segment of FIG. 6

Each buccal segments 22a, b also includes a rest 34a,b as best shown in FIGS. 2A, 5 and 6A. These rests 34a,b are 0.036 inch×0.072 inch annealed wires connected to the feet 24 to extend horizontally and anteriorly in order to closely overlay the facial surfaces of the cuspids. These rests 34a,b are bonded to the cuspid by conventional bonding techniques and are adapted to stabilize the mandibular component 15 against vertical and torsional forces generated by the links 16 during the forward jaw posturing of the mandible. The facial rests 34a, b also stabilize the mandibular component 15 against elevating forces generated by the incisor intrusion wire referred to below and, where the appliance 10 incorporates an expansion screw for arch development, the facial rests 34a, b resists vertical forces inherent to the inclined plane of the lingual surface of the cuspid.

To provide for intrusion of the anterior teeth, a wire (not shown) is inserted into bores 30 at the facial ends 28a of the feet 24 and is locked therein by frictional forces and is coupled to braces 36 as best shown in FIG. 2B. In that the intrusion forces generated by the wire and transmitted to the feet 22a, b include a vertical lifting component, the facial rests 34a, b resist the vertical forces. The forward directed vectors of these forces are resisted by a molar band 46 (FIG. 3) and the rests 34a,b. Torsion about the apex 27 is resisted by the rests 34a, b and the coupling of the lingual extensions 26 to the molar band 46 as hereinafter described.

Figure 10:
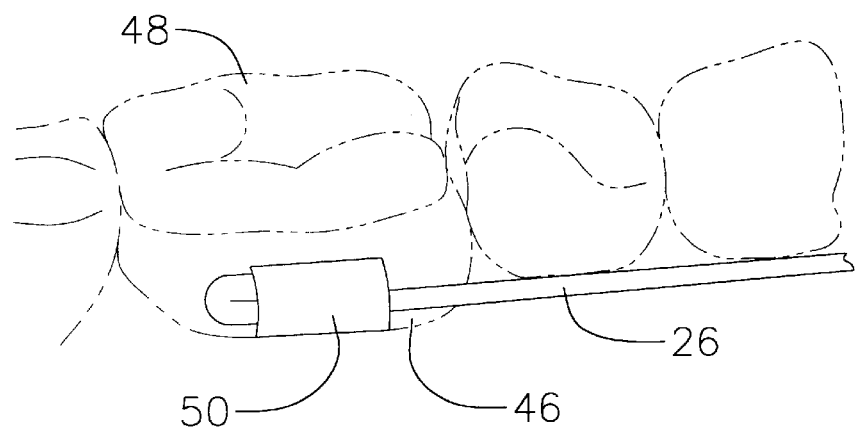
FIG. 10 shows a molar band, lingual view, for the lower support structure.
Figure 11A:
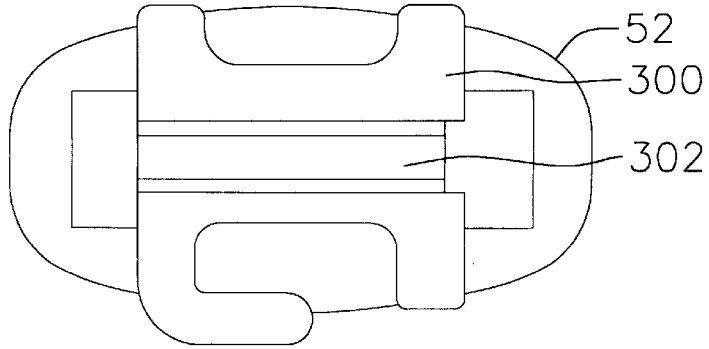
FIG. 11A shows a side view of the molar band for the maxillary component.
Figure 11B:
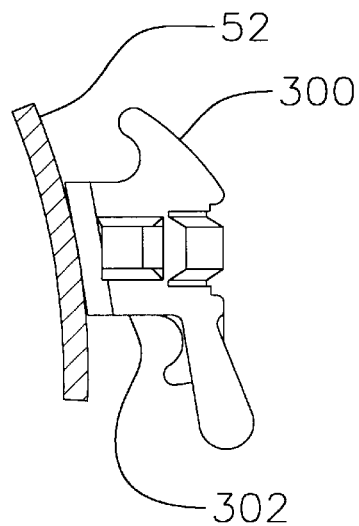
Figure 12:
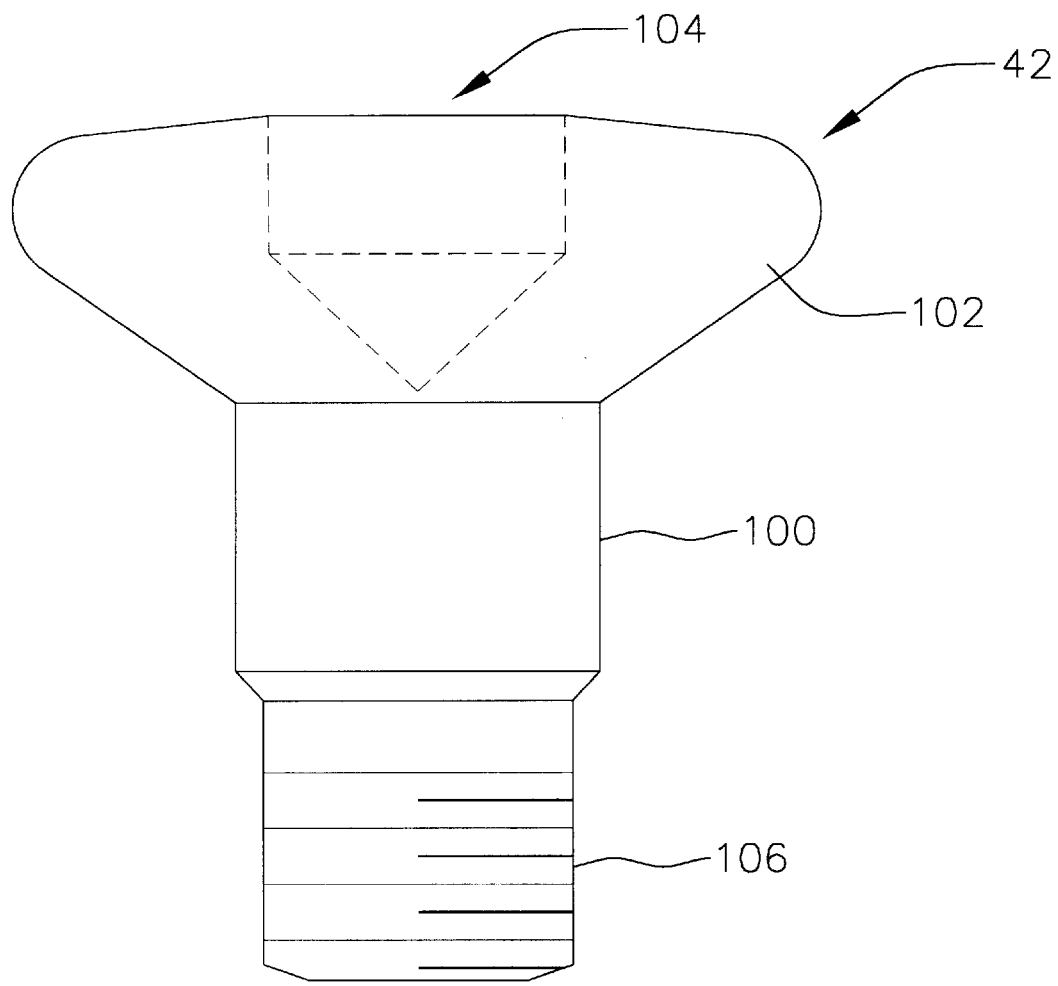
FIG. 12 shows a screw hub for use in the appliance.

As shown in FIGS. 6A and 10, each foot 24 includes a tapped and threaded bore 40 approximately 2 mm from the facial end 28a and is adapted to receive a screw hub 42 (FIGS. 2B, 3, 4, and 12) defining one axle 44a for an end of a link 16. The screw hub 42, as shown in FIG. 12, has a smooth shank 100 defining the hub upon which the end of the links 16 can pivot and an enlarged head 102 which tapers to the shank 100 to provide for a degree of pivot of the links 16 about the shank. The head 102 has an axial, hexagonal receiver 104 to receive a tool for rotating the screw hub 42 to secure it to the feet 24. Opposite the head 102, the screw hub 42 has threads 106 to be received in the threaded bore 40.

Turning to FIGS. 2A, 3, and 10, the mandibular component 15 also includes a molar band 46 secured upon a molar 48 as by a mechanical interference fit and/or bonding. The molar band 46 may be of a currently known and used type. On the lingual circumference of the molar band 46 is a sheath 50 selected to receive and secure the lingual extension 26 as shown in FIG. 10. The insertion of the lingual extension 26 into the sheath 50 provides vertical and lateral stability and is constructed to allow anteroposterior adjustability that facilitates location of the feet 24 precisely in the embrasure of the cuspid and first bicuspid or first deciduous molar and furthermore facilitates easy removal of the entire unit upon completion of the designated therapeutic application.

Figure 4:
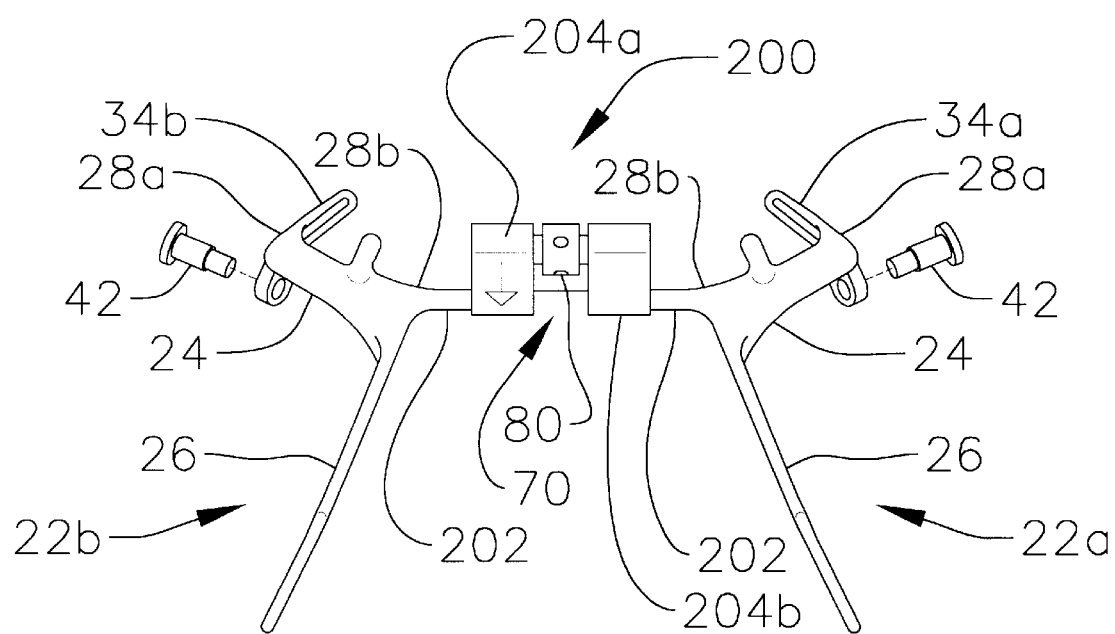
FIG. 4 is a top view of the mandibular component.

By providing the screw hub 42, the mandibular component 15 can be positioned incrementally. Heretofore, projecting hubs for prior Herbst devices would irritate the inside of the cheek. By providing the threaded bore 40 and screw hub 42, when the links 16 are not positioned, the screw hubs 42 can be removed presenting a smooth and low profile surface on the outside of the feet 24, thereby eliminating buccal tissue irritation.

Where only Herbst therapy is to be employed, with reference to FIG. 5, a support 51 connects the feet 24 and is arcuate to proximate the gingival line on the lingual of the front teeth to be unobtrusive.

Where Herbst therapy is to be combined with mandibular arch development to widen the arch, the mandibular component 15 includes a lower expansion mechanism 200 as shown in FIGS. 3 and 4. Expansion results in arch development and thereby creates space to resolve the crowding of the teeth.

The mandibular expansion mechanism 200 includes a pair of legs 202 each having one end connected to an end 28b of each foot 24 as by soldering. The legs 202 reside behind the front teeth to position a pair of screw blocks 204a,b. To maintain alignment between the screw blocks 204a,b a pair of guide rods 70 cooperatively pass through the screw blocks 204a,b which are free to move along the rods 70 and to be guided thereby. Disposed between the screw blocks 204a,b is a screw 80 (FIG. 4) which is reversely threaded and received in threaded and tapped bores in the screws blocks 204a,b. Rotation of the screw 80 urges the screw blocks 204a,b apart which, through the legs 202 imposes an expansion force upon the feet 24 to reconfigure the lower arch in the desired manner.

Turning to FIGS. 2A, 7–9, 11A, B and 13 the maxillary component 14 includes a pair of stainless steel molar bands 52 (FIG. 18) which are cemented to the molars and are of conventional design. Each molar band 52 includes on its buccal surface a buccal tube 300 having a web 302 supporting the tube spaced from the band 52. As hereinafter described, the buccal tubes 300 provide for coupling of the bucco-occlusal segments 308 to each molar band 52.

Returning to FIGS. 2, 7–9, to provide for support of the upper ends of the links 16, and more particularly the tubes 18 thereof, the maxillary component 14 includes the bucco-occlusal segments 308. The buccal-occlusal segments 308 are disposed at opposite sides of the mouth and include feet 310 consisting of two lengths of 1.5 mm×3.0 mm oval wire bent in the middle over its narrow dimension to approximately 90 degrees to project to the occlusal tooth surfaces. Coupled to each foot 310 there is included an anterior and posterior extending occlusal rest 54 which is positioned to be bonded to the occlusal surfaces of the molars as well as the first and second bicuspids and/or first and second deciduous molars. The rest 54 augments fixation of the buccal-occlusal segments 308 to the stainless steel molar band 52 to the teeth, acts to tie the entire buccal quadrant together and provides efficient tooth borne resistance to ensure palatal splitting as opposed to lateral tipping of the teeth. Further each rest 54 and the cement that covers it opens the bite by creating higher occlusion which delivers an intrusive force to the buccal segments that, in turn, resists extrusion of the buccal segments inherent to the expansion mechanics. Each rest 54 further ties buccal segments together to resist tooth movement during bite jumping activation which enhances the desired orthopedic effects. Still further, the rests 54 help resist distal tipping of the first molar caused by torsion during bite jumping and to tie the terminal molar to the more anterior teeth of the buccal segments during arch expansion as hereinafter described.

Also secured to each foot 310 opposite the rest 54 at the exterior surface thereof is a forwardly extending buccal extensions 56. The buccal extensions 56 extend anteriorly along the facial surfaces of the bicuspid and/or deciduous molars and the cuspids. At the ends of the buccal extensions 56 are hooks 35 and tubes 33 with 0.030 mm lumen intended to receive orthodontic arch wire which is secured in braces on the maxillary incisors.

Figure 1:
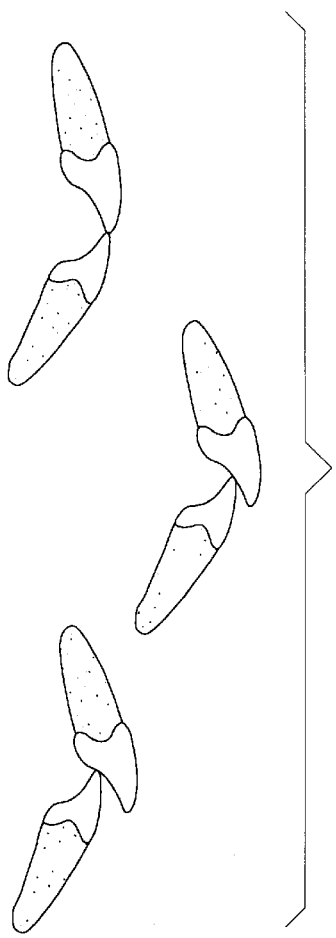
FIG. 1 illustrates 0, 30% and 70% overbite with accompanying depiction of increasing overjet.

The buccal extensions 56 have several purposes. They are connected elements which tie the anterior to the posterior teeth. They further facilitate delivery of neutral, intrusive and extrusive forces to the anterior teeth through any braces coupled thereto. The most common adjustment is intrusion in order to minimize the occurrence of the adverse incline plane as shown in FIG. 1. Further they allow for forward positioning of a threaded bore 40 on the feet 310.

Each foot includes the threaded bore 40 to receive the screw hubs 42 which define axles 44 for the opposite ends of the links 16. The buccal surface of the molar bands 52 with attached screw hubs 42 present a profile that is minimal to thereby eliminate irritation of buccal mucosa during those stages of treatment when the links 16 and screw hubs 42 are not in place. The location of the threaded bores 40 on the anterior of the feet 310 provide several advantages. This location facilitates fixation of the links 16 and screw hubs 42 insertion by allowing easier access for the operator and more comfort to the patients since less lip commissure retraction is required for access. Further this location affords greater patient comfort by creating more clearance between the mucosa covering the exterior oblique ridge below the coronoid process which moves forward and approximates the upper terminal molar during lower jaw forward posturing. When in place and to provide sufficient length so that the rods 18 do not disengage from the tubes 20 the rods 18 must extend beyond the end of the tubes 20 where they couple with and are connected by the screw hubs 42. In earlier device designs where screw mechanisms were located posteriorly on the molar, the rod extension would often impinge the tissue of the forward postured oblique ridge resulting in lesions and discomfort. Attempts to shorten the rod to stop the lesions made the rod so short that the rod and tube would disengage during extreme openings such as when one yawns. The forward positioning of the threaded bores 40 and screw hubs 42 on the molar bands 52 allows enough rod extension to prohibit disengagement without irritating the mucosa.

Figure 13:
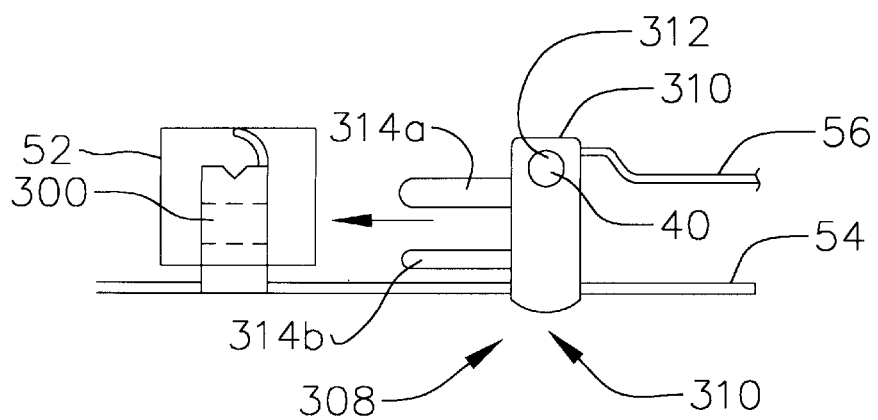
FIG. 13 shows the coupling of the bucco-occlusal segment to the molar band.

To couple the feet 310 to the molar bands 52, each foot 310 includes a pair of spaced tines 314a, b (FIG. 9) adapted to span the web 302 of the molar buccal tube 300. Thus, after fixation of the molar band 52, the foot 310 is coupled to the band 52 by sliding the tines 314a, b between the buccal tube 300 and band 52 to span the web 302 as suggested in FIG. 13. Bonding the occlusal rests 54 of the buccal occlusal segments 308 to the occlusal surfaces of the teeth ties the maxillary component 14 together.

Figure 15A:
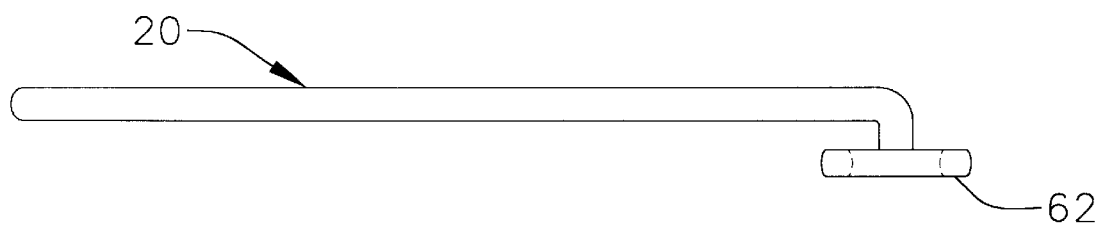
FIGS. 15A and 15B show orthogonal views of the rods for the Herbst therapy links.
Figure 15B:
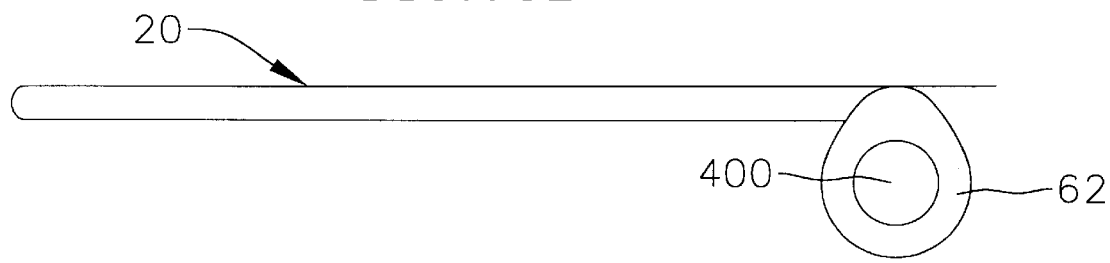

Turning to FIGS. 2A, 2B, and 15A, B each link 16 includes the rod 20 having at an end an offset eye 62, the offset being from the axis of the rod 20. The offset provides clearance of the links 16 from the buccal surfaces of the lower teeth and from the lower molar band 46. Each eye 62 includes a bore 400 to closely pass the screw hubs 42 to secure the rods 20 to the buccal segments 22a, b of the mandibular component 14. The rods 20 are free to pivot about the screw hubs 42 to accommodate opening and closing of the mouth. To permit a degree of rocking of the rods 20, each bore 400 may be hyperbolic as best shown in FIG. 15A.

Figure 14A:
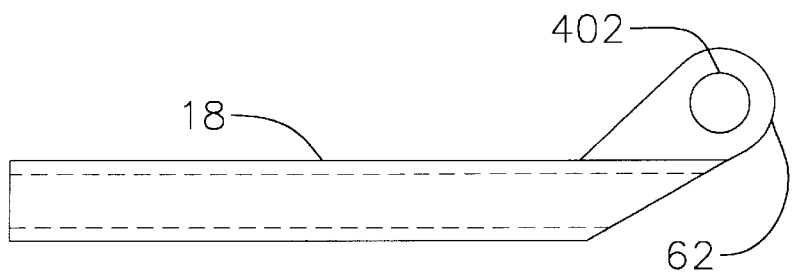
FIGS. 14A–C show various views of the tubes for the Herbst therapy links.
Figure 14C:
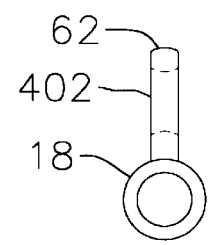
Figure 14B:
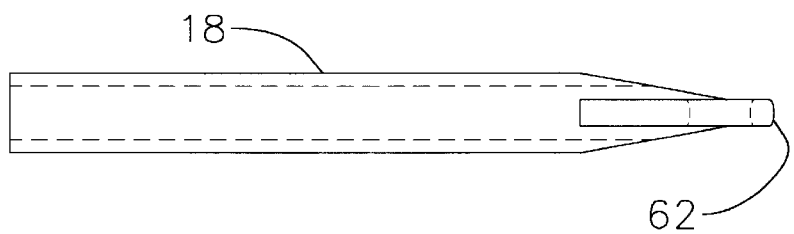

The tubes 18 also include eyes 62 as best shown in FIGS. 14A–C. The eyes 62 include a bore 402 to closely pass the screw hubs 42 to secure the tubes 18 to the maxillary component 14 to permit it to pivot thereabout. To permit a degree of rocking of the tubes 18, each bore may be hyperbolic as best shown in FIG. 14B.

For Herbst therapy the mandibular component 15 and maxillary component 14 are assembled and mounted as described above and as shown in FIGS. 2A, B. The links 16 are assembled and are coupled by the insertion of the screw hubs 42 through the eyes 62 of the links 16 at both sides of the mouth. Accordingly, the links 16 and maxillary and mandibular components 14,15 exert no influence on opening and closing motion, but only on the ultimate position of the mandible 12 relative to the maxilla.

Turning to FIG. 7, the appliance 10 further includes an upper expansion mechanism 64 which forms an integral part of the bite-jumping therapy based on the need to coordinate the dental arches that are elliptical in form. The relationship between a dental arch and an elliptical arch is such that the posterior teeth (pre-molars and molars) correspond to the legs of an elliptical arch and the anterior teeth (cuspids and incisors) correspond to the anterior portion of the arch surrounding the crest or apex. The relationship of dental arches in a Class II (overjet) dysplasia is such that the legs of the respective arches coincide posteriorly with the apex of the lower arch lying deep within the perimeter of the upper arch which creates the overjet effect. When the maxilla and mandible are in this relation they represent two elliptical arches with different foci. A bite-jumping device corrects overjet by forward posturing the mandible so that the apicies of the two elliptical arches (upper and lower arches) overlay and coincide. When the forward posturing occurs the posterior elliptical arch legs no longer coordinate because the lower arch now overlays a narrower portion of the upper arch. For coordination of the two dental arches to occur, the upper arch must be made wider to coincide with the now forward-postured lower arch. The upper expansion mechanism 64 accomplishes this task by widening the posterior teeth thereby changing the shape of the upper elliptical arch.

The upper expansion mechanism 64 serves one other purpose which is directed to the crowding of teeth. Expansion results in arch development and thereby creates space to resolve the crowding. As with the maxillary and mandibular components 14, 15 and the links 16 which provides dual benefit of forward posturing the mandible and intruding the teeth, the expansion mechanism 64 treats the overjet dysplasia and minimizes multiple appliance exposures to the patient.

The upper expansion mechanism 64 includes a pair of frames 66 each having one end connected to the molar bands 52 as by soldering and to the other end one of a pair of screw blocks 68a,b. The frames 66 are arcuate and curved to approximate the roof of the mouth and to position the screw blocks 68a,b proximate the roof of the mouth. To maintain alignment between the screw blocks 68a,b a pair of guide rods 70 cooperatively pass through the screw blocks 68a,b which are free to move along the rods 70 and to be guided thereby. Disposed between the screw blocks 68a,b is a screw 80 which is reversely threaded and received in threaded and tapped bores in the screws blocks 68a,b. Rotation of the screw 80 urges the screw blocks 68a,b apart which, through the frames 66 imposes an expansion force upon the crowns 52 to reconfigure the upper arch in the desired manner.

The appliance 10 as described above is able to address the dilemma of adverse overbite. Since the bores 30 are located on the feet 24 (mandibular component 15) inferior to the occlusal plane, the attached wire delivers through the braces 36 an intrusive force upon the incisors. Intruding the incisors separates them vertically from their antagonist, the upper incisors, and thereby decreases overbite and, hence no adverse inclined plane can result to destroy what the bite jumping appliance 10 achieved.

Further, the appliance 10 is more patient tolerable and comfortable. The same molar bands 46, 52 can be used for all orthodontic treatment protocols. Heretofore, the molar anchoring devices, in this case stainless steel molar crowns, were an integral part of the bite-jumping appliance; therefore, when the overjet correction was complete and it became time to remove the bite-jumping hardware, the molar attachments were also removed. In most instances, these molar teeth are very sensitive following such therapy and removing the attaching devices may be mildly to significantly uncomfortable to patients. When another molar attachment is applied as part of the "normal braces hardware," the tooth is again traumatized and the patient re-endures the process. The apparatus 10 according to present invention can be removed by mechanically removing the bonding cement from the feet 24, rests 34a (mandibular component 15 and occlusal rests 54 (maxillary component 14) and the entire unit is dislodged by simply sliding the buccal segments 22a, b forward to disengage the lingual extensions 26 from the sheaths 50 of the molar bands 46 and by sliding the bucco-occlusal segments 308 forward to disengage the tines 314a, b from the webs 302 of the molar bands 52. There is significantly less discomfort on appliance removal and the molar is not subjected to the application of more hardware. Not only is the patient spared the discomfort but what also once required at least two if not more appointments now requires just one thereby decreasing overall treatment time.

Further, the manner in which the mandibular component feet 24 nestle into the embrasure between the cuspid and first pre-molar or the first deciduous molar results in a profile that is much less protrusive than previous designs. The fact that the feet 24 pass from the lingual to the facial over the occlusal surface and in the embrasure is what allows such a low profile. The benefit of such a profile is that there is less irritation to the buccal mucosa of the cheek and lip; and therefore, much more comfort to the patient. Furthermore, and by virtue of the tapped and threaded bore 40 which receives the screw hubs 42, there is no axle protruding from the buccal segments 22 to irritate the patient during those times when the links 16 are not engaged.

Further, the cementing mechanism used to secure the rests 34a,b on the facial and lingual surfaces of the cuspid is called "bonding." Bonding is a process in which a mild acid solution is applied to the enamel surface of the tooth for some seconds to etch the enamel and create microscopic porosity. A sealer is then applied to the etched surfaces. The sealer is a liquid part of the cement and it bonds mechanically to the porous surface created by the etching. Following the sealing, bonding cement (actually this cement is the same as a liquid but has "fillers" which make the cement stiffer so that it can be molded to the user's desire) is applied and cements the rests 34a,b and 54 directly to the tooth surfaces. There is no other cementing procedure more comfortable to a patient than bonding; and bonding, as opposed to cementing procedures of years past, brings attachment of bite-jumping appliances into the most modern era.

Furthermore, the multi-functional nature of the appliance 10 as heretofore mentioned relative to the lower and upper arch development with the upper and lower expansion mechanisms 64, 200 in addition to its ability to correct Class II dysplasia either orthopedically or dentally, subjects the patient to just one application which in the past required multiple appliances.

Still further, based upon the premise that human tooth size is relatively consistent, and that the lateral and anteroposterior adjustability can be built into both the mandibular and maxillary components 15, 14 by simply extending the length of the lingual extensions 26 and left and right bucco-occlusal segments 308 such that the appliance 10 can be pre-assembled and delivered in kit form. The obvious benefit of pre-assembled units is that less laboratory time is required to make them patient ready. The only in-office assembly required is to add expansion mechanisms 64, 200 for arch development and arch coordination.

Further the entire appliance can be delivered in a kit form and can be used in conjunction with upper and lower braces and tied thereto to provide a uniform, consistent assembly. Further the appliance 10 and kit, according to the preferred embodiment, uses conventional and available molar bands and expansion mechanisms.

While I have shown and described certain embodiments of the present invention, it is to be understood that it is subject to many modifications without departing from the scope of the claims.

I claim:

1. An orthodontic appliance to provide for Herbst therapy comprising:

a mandibular component including left and right buccal segments each including an arcuate foot adhered to the teeth over the occlusal embrasure between the cuspid and first bicuspid, each foot including a threaded bore in the facial surface thereof;

a maxillary component including left and right bucco-occlusal segments each including a foot which is adhered to the teeth over the occlusal embrasure proximate the first molar and extending to the buccal side of the teeth, each bucco-occlusal segment having on said buccal side a threaded bore;

screw axles threadably and removably disposed in said threaded bores and pivotally mounting the ends of rod and tube links which couple the mandibular and maxillary components to reposition the mandible.

2. The appliance of claim 1 wherein said screw axles include a shank having a threaded end to be threadably received into said threaded bores and a hub to pivotally mount an end of a rod or tube.

3. The appliance of claim 1 wherein said mandibular buccal segments include on the lingual side thereof posteriorly extending lingual extensions coupled to a molar band fixed to a molar.

4. The appliance of claim 1 wherein each buccal segment includes a facially extending rest positioned to be adhered to a cuspid.

5. The appliance of claim 1 wherein each buccal segment includes on the inferior-facial portion of the foot a bore to receive a wire coupled to braces.

6. The appliance of claim 1 including an expansion mechanism coupled between the mandibular component feet to reconfigure the mandibular arch.

7. The appliance of claim 1 wherein the maxillary component includes molar bands fixed to molars, each molar band including a buccal tube supported on a web and each bucco-occlusal segment includes tines to couple the bucco-occlusal segment to the molar band web.

8. The appliance of claim 7 wherein each bucco-occlusal segment includes forwardly extending tubes and hooks for coupling to brace wire.

9. The appliance of claim 1 including an expansion mechanism disposed between said bucco-occiusal segments to reconfigure the maxillary arch.

10. An orthodontic kit for providing bite jumping therapy, arch development and for supporting a brace structure comprising:

a mandibular component including left and right buccal segments each including (i) an arcuate foot adhered to the teeth over the occlusal embrasure between the cuspid and first bicuspid, each foot including (a) a threaded bore in the facial surface thereof and (b) a forwardly directed bore attachment to brace wire, (c) a rest to be adhered to the facial surface of the incisors and (d) lingual extensions to extend posteriorly, (ii) molar bands to be coupled to bracing wire and including sheaths for coupling with lingual extensions and (iii) an expansion mechanism for mandibular arch development coupled between said buccal segments;

a maxillary component including (i) molar bands each including a buccal tube supported on a web (ii) left and right bucco-occlusal segments each including (a) rests to be adhered to occlusal surfaces and (b) a foot which extending to the buccal side of the teeth, each segment having on said buccal side a threaded bore and a pair of tines to couple the buccal-occlusal segments to the molar bands and (c) an expansion mechanism disposed between said molar bands for maxillary arch development;

rod an tube links; and screw axles threadably and removably disposed in said threaded bores and pivotally mounting the ends of the rod and tube links which couple the mandibular and maxillary components to reposition the mandible.

* * * * *